United States Patent [19]

Fuse

[11] Patent Number: 5,115,349
[45] Date of Patent: May 19, 1992

[54] PROJECTOR SYSTEM AND SYSTEM FOR DETECTING FLAW

[75] Inventor: Jiro Fuse, Kasukabe, Japan

[73] Assignee: Kabushiki Kaisha Machida Seisakusho, Tokyo, Japan

[21] Appl. No.: 526,136

[22] Filed: May 22, 1990

[30] Foreign Application Priority Data

May 25, 1989 [JP] Japan .................................. 1-130256
May 25, 1989 [JP] Japan .................................. 1-130257

[51] Int. Cl.⁵ .......................... G02B 3/04; G02B 6/06; G01N 21/00
[52] U.S. Cl. .................................. 358/709; 359/619; 385/116; 356/237; 356/241
[58] Field of Search ................. 350/431-435, 350/96.18, 96.25, 96.26, 96.28, 169-174, 320-321, 96.1, 96.15, 96.23, 96.25; 36 D/11, 32, 227, 234, 252; 356/237-241, 355-359, 445-446

[56] References Cited

U.S. PATENT DOCUMENTS

| | | |
|---|---|---|
| 3,964,824 | 6/1976 | Dixon .................................. 350/433 |
| 4,184,748 | 1/1980 | Kugler et al. ......................... 350/433 |
| 4,427,265 | 1/1984 | Suzuki et al. ........................ 350/321 |
| 4,521,087 | 6/1985 | Hayes ................................... 350/574 |
| 4,623,776 | 11/1986 | Buchroeder et al. ............... 350/172 |
| 4,793,694 | 12/1988 | Liu ....................................... 350/170 |
| 4,826,269 | 5/1989 | Streifer et al. ....................... 362/252 |

FOREIGN PATENT DOCUMENTS

| | | |
|---|---|---|
| 53-133048 | 11/1978 | Japan . |
| 54-21073 | 7/1979 | Japan . |
| 235813 | 10/1986 | Japan .................................. 350/169 |
| 63-80220 | 4/1988 | Japan . |

Primary Examiner—Bruce Y. Arnold
Assistant Examiner—Thong Nguyen
Attorney, Agent, or Firm—Fish & Richardson

[57] ABSTRACT

A projector system includes an optical converter element of a cylindrical shape, and a light beam-generating device for generating a plurality of light beams. Optical axes of the plurality of light beams are spaced from one another in a direction of the circumference of the optical converter element and intersecting one another substantially at one point lying on the axis of the optical converter element. The optical axes of the plurality of light beams are inclined at the same angle with respect to the axis of the optical converter element, so that when the plurality of light beams are incident on the optical converter element, an outgoing light beam is emitted from the optical converter element in such a manner that the outgoing light beam extends along an imaginary conical surface coaxial with the optical converter element. This outgoing light beam can be converted by a collimator lens into a light beam extending along an imaginary cylindrical surface. The light beam extending along the imaginary conical surface or the imaginary cylindrical surface is applied to an annular portion of an object to be detected, so that part of this light beam leaking through a flaw in the annular portion is detected by a photosensor.

14 Claims, 2 Drawing Sheets

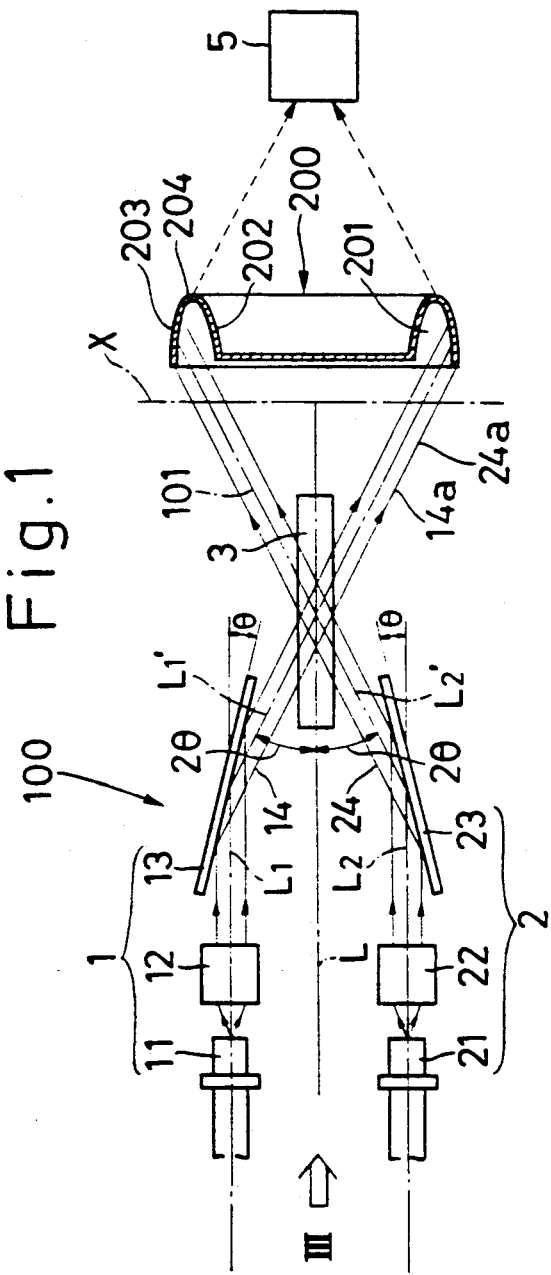
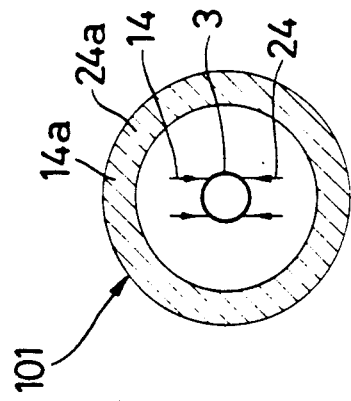
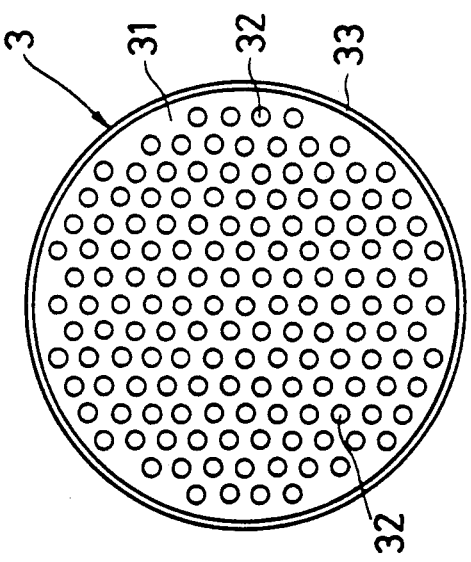

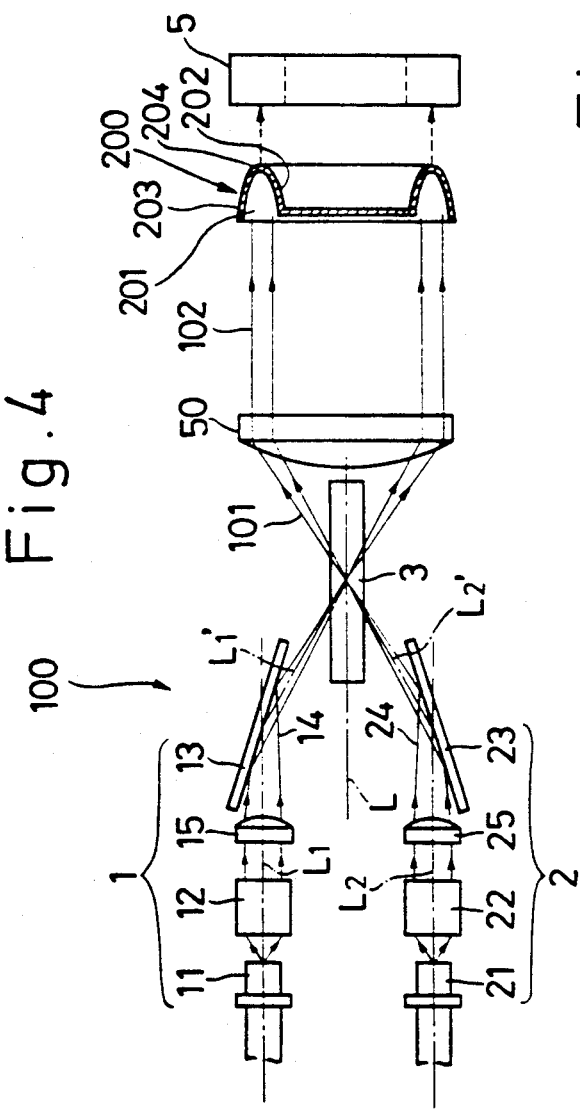
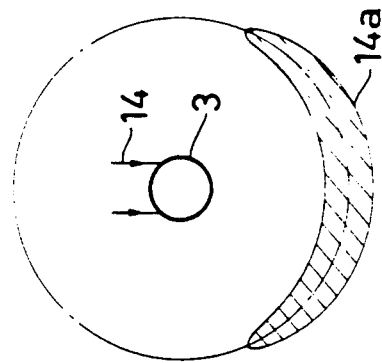
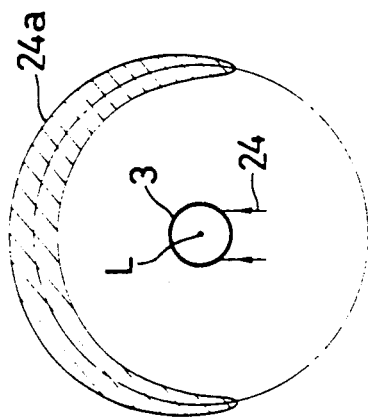
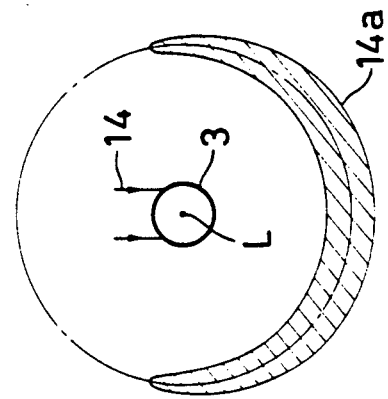

PROJECTOR SYSTEM AND SYSTEM FOR DETECTING FLAW

BACKGROUND OF THE INVENTION

This invention relates to a projector system for supplying a light beam capable of forming a ring-shaped image on a plane, and also to a system for detecting a flaw in an annular portion of an object, using such a projector system.

A projector system, disclosed in Japanese Laid-Open (Kokai) Patent Application No. 80220/88 (corresponding to U.S. patent application Ser. No. 100,523 now abandoned), includes a cylindrical fiber conduit (optical converter element) comprising a number of parallel optical fibers. When a light beam is caused to be incident upon the fiber conduit in a direction perpendicular to the axis of the fiber conduit, a light beam radiating in a plane perpendicular to the axis of the fiber conduit is emitted from the fiber conduit. This outgoing light beam appears as a linearly-extending image on a plane parallel to the axis of the fiber conduit.

The above Japanese Laid-Open Patent Application No. 80220/88 discloses another prior art projector system in which a cylindrical lens is used as an optical converter element.

U.S. Pat. No. 3,964,824 discloses a projector system similar to that described in the above Japanese Laid-Open Patent Application No. 80220/88.

Japanese Laid-Open Patent Application No. 133048/78 discloses a projector system which comprises a light source, and a pair of first and second cylindrical lenses. A light beam generated from the light source is incident on the first cylindrical lens in a direction perpendicular to the axis of the first cylindrical lens. As a result, the light beam, spreading out at a certain angle in a plane perpendicular to the axis of the first cylindrical lens, is emitted from the first cylindrical lens. This outgoing light beam is converged in the direction of the axis of the first cylindrical lens by the second cylindrical lens whose axis is inclined relative to the axis of the first cylindrical lens.

All of the above conventional projector systems are designed to supply the light beam which appears as a linear image on the plane.

In a projector system disclosed in Japanese Utility Model Publication No. 21073/79, a light beam, advancing along a thin band-like path, is caused to be incident on a cylindrical lens in a direction inclined relative to the axis of the cylindrical lens. As a result, the light beam emitted form the cylindrical lens spreads out along part of an imaginary conical surface, and forms an arc-shaped image in a certain plane; however, this image is not in the form of a complete or closed circle.

SUMMARY OF THE INVENTION

It is a first object of this invention to provide a projector system for supplying a light beam capable of forming a closed ring-shaped image in a certain plane.

A second object of the invention is to provide a system for detecting a flaw in an annular portion of an object to be detected, using the above projector system.

In order to achieve the first object, according to one aspect of the present invention, there is provided a projector system comprising:

(a) an optical converter element of a cylindrical shape for converting incident light, applied thereto, into outgoing light spreading out radially of the optical converter element; and (b) light beam-generating means for generating a plurality of light beams, optical axes of the plurality of light beams being spaced from one another in a direction of the circumference of the optical converter element and intersecting one another substantially at one point lying on the axis of the optical converter element, and the optical axes of the plurality of light beams being inclined at the same angle with respect to the axis of the optical converter element, so that when the plurality of light beams are incident on the optical converter element, an outgoing light beam is emitted from the optical converter element in such a manner that the outgoing light beam extends along an imaginary conical surface coaxial with the optical converter element.

In order to achieve the second object, according to another aspect of the invention, there is provided a system for detecting a flaw in an annular portion of an object to be detected, comprising:

(a) an optical converter element of a cylindrical shape for converting incident light, applied thereto, into outgoing light spreading out radially of the optical converter element;

(b) light beam-generating means for generating a plurality of light beams, optical axes of the plurality of light beams being spaced from one another in a direction of the circumference of the optical converter element and intersecting one another substantially at one point lying on the axis of the optical converter element, and the optical axes of the plurality of light beams being inclined at the same angle with respect to the axis of the optical converter element, so that when the plurality of light beams are incident on the optical converter element, an outgoing light beam is emitted from the optical converter element in such a manner that the outgoing light beam extends along an imaginary conical surface coaxial with the optical converter element; and (c) a photosensor disposed on one side of the optical converter element opposite to the light beam-generating means, the object to be detected being disposed between the optical converter element and the photosensor, the outgoing light beam emitted from the optical converter element being applied to the annular portion of the object, so that the photosensor detects part of the outgoing beam leaking through the flaw in the annular portion.

Also, in order to achieve the second object, according to a further aspect of the invention, there is provided a system for detecting a flaw in an annular portion of an object to be detected, comprising:

(a) an optical converter element of a cylindrical shape for converting incident light, applied thereto, into outgoing light spreading out radially of the optical converter element;

(b) light beam-generating means for generating a plurality of light beams, optical axes of the plurality of light beams being spaced from one another in a direction of the circumference of the optical converter element and intersecting one another substantially at one point lying on the axis of the optical converter element, and the optical axes of the plurality of light beams being inclined at the same angle with respect to the axis of the optical converter element, so that when the plurality of light beams are incident on the optical converter element, an outgoing light beam is emitted from the optical converter element in such a manner that the outgoing light beam extends along an imaginary conical surface coaxial with the optical converter element; and (c) a collimator lens disposed on one side of the optical converter element opposite to the light beam-generating means, the collimator lens being coaxial with the optical converter element, the focus of the collimator lens lying substantially on the apex of the imaginary conical surface, and when the light beam emitted from the optical converter element along the imaginary conical surface is incident on the collimator lens, a light beam being emitted from the collimator lens along an imaginary cylindrical surface coaxial with the collimator lens; and (d) a photosensor disposed on one side of the collimator lens opposite to the optical converter element, the object to be detected being disposed between the collimator lens and the photosensor, the light beam emitted from the collimator lens being applied to the annular portion of the object, so that the photosensor detects part of the light beam leaking through the flaw in the annular portion.

BRIEF DESCRIPTION OF THE DRAWINGS

FIG. 1 is a schematic view of a flaw detecting system provided in accordance with the present invention;

FIG. 2 is an enlarged, transverse cross-sectional view of an optical converter element used in the system;

FIG. 3 is a view of the optical converter element as seen from the direction III of FIG. 1, showing an image formed on an imaginary plane by a light beam emitted from the optical converter element;

FIG. 4 is a view similar to FIG. 1, but showing a modified system;

FIGS. 5 and 6 are views similar to FIG. 3, but showing a modified optical converter element, these Figures respectively showing images respectively formed on the imaginary plane by light beams emitted from the optical converter element when light beams are incident on diametrically-opposite points of the optical converter element; and FIG. 7 is a view similar to FIG. 3, but showing another modified optical converter element, this Figure showing an image formed on an imaginary plane by a light beam emitted from the optical converter element when a light beam is incident on the optical converter element in one direction.

DESCRIPTION OF THE PREFERRED EMBODIMENTS OF THE INVENTION

The invention will now be described with reference to the drawings.

FIG. 1 shows a flaw detecting system using a projector system 100. The projector system 100 comprises two laser beam-generating devices 1 and 2, and an optical converter element 3.

One laser beam-generating device 1 comprises a semiconductor laser diode 11, a collimator lens 12 and a reflection mirror 13 which are arranged in this order in a forward direction. The laser diode 11 and the collimator lens 12 have a common optical axis L1. The laser diode 11 emits a laser beam spreading out into a conical shape. The collimator lens 12 converts the laser beam, emitted from the laser diode 11, into a laser beam of a uniform circular cross-section along a length thereof, the latter laser beam extending along the optical axis L1 and being composed of parallel rays of laser light. Therefore, the laser diode 11 and the collimator lens 12 cooperate with each other to constitute a light source for providing the parallel rays of laser light. The reflection mirror 13 is inclined at an angle $\theta$ ($0° < \theta < 45°$) with respect to the optical axis L1. Therefore, an optical axis L1' of a laser beam 14 reflected by the reflection mirror 13 is inclined at an angle of $2\theta$ with respect to the optical axis L1.

The other laser beam-generating device 2 is of the same construction as that of the above laser beam-generating device 1. Namely, the laser beam-generating device 2 comprises a semi-conductor diode 21, a collimator lens 22, and a reflection mirror 23. A common optical axis L2 of the laser diode 21 and the collimator lens 22 is parallel to the optical axis L1. A laser beam 24 is equal in diameter to the laser beam 14. The reflection mirror 23 is inclined with respect to the optical axis L2 at the same angle as the inclination angle $\theta$ of the reflection mirror 13. Reflecting surfaces of the two reflection mirrors 13 and 23 face each other. With this arrangement, the optical axes L1' and L2' of the laser beams 14 and 24 reflected respectively by the reflection mirrors 13 and 23 intersect each other at a point disposed centrally of the distance between the optical axes L1 and L2.

The optical converter element 3 is referred to as "fiber conduit". As shown in FIG. 2, the optical converter element 3 has a cylindrical shape, and comprises a clad 31, a large number of optical fibers 32 of a circular cross-section embedded in the clad 31 and extending parallel to an axis L of the optical converter element 3, and a protective glass shell 33 covering the outer periphery of the clad 31. The clad 31 is greater in diameter than the laser beams 14 and 24. The relation between refractive indexes n1, n2 and n3 of the clad 31, the optical fibers 32 and the protective glass shell 33 is as follows:

$$n_3 \leq n_1 < n_2$$

The axis L of the optical converter element 3 passes through the point of intersection between the optical axes L1' and L2' of the laser beams 14 and 24 reflected respectively by the reflection mirrors 13 and 23. The axis L of the optical converter element 3 is parallel to the optical axes L1 and L2, and these three axes lies in a common plane. Therefore, the optical axes L1' and L2' of the laser beams 14 and 24 coming respectively from the reflection mirrors 13 and 23 are spaced 180° from each other circumferentially of the optical converter element 3, that is, disposed in diametrically-opposite relation to each other with respect to the optical converter element 3. The axes L1' and L2' are both inclined at the same angle of $2\theta$ ($0° < 2\theta < 90°$) with respect to the axis L of the optical converter element 3. In other words, the laser beams 14 and 24 are incident on the optical converter element 3 at an inclination angle of $2\theta$.

Although one hundred and several tens of optical fibers 32 are shown in FIG. 2 for illustration purposes, actually each optical fiber 32 has a diameter very much narrower than the illustrated diameter thereof, and the number of the optical fibers 32 are several tens of thousands.

In the projector system 100 of the above construction, when one laser beam 14 (the upper one in the drawings) is incident on the clad 31 of the optical converter element 3, this incident laser beam is repeatedly refracted and reflected at the boundaries between the clad 31 and the optical fibers 32. As a result, a laser beam 14a is emitted from the optical converter element 3 in such a manner that this laser beam 14a spreads out progressively from the entire periphery of the optical converter element 3. Since the laser beam 14 is incident on the optical converter element 3 in inclined relation to the axis L of the optical converter element 3, the rays of the outgoing laser beam 14a are also inclined at the same angle with respect to the axis L. Therefore, the outgoing laser beam 14a spreads out along an imaginary conical surface. This conical surface is coaxial with the optical converter element 3, and its apex lies substantially at the point of intersection between the optical axes L1' and L2'.

A circular image (indicated by hatching in FIG. 3) is formed by the laser beam 14a, emitted from the optical converter element 3, on an imaginary plane X disposed forwardly of the optical converter element 3 in perpendicular relation to the axis L of the optical converter element 3.

The lowermost portion of the laser beam 14a is the highest in light intensity whereas the uppermost portion of the laser beams 14a is the lowest. In other words, the lowermost portion of the image appearing on the imaginary plane X is the brightest whereas the uppermost portion of the image is the darkest.

When the other laser beam 24 (the lower one in the drawings) is incident on the optical converter element 3, a laser beam 24a is emitted from the optical converter element 3 and spreads out progressively along the above-mentioned conical surface. In contrast with the laser beam 14a, the laser beam 24a is the highest in light intensity at its uppermost portion, and is the lowest at its lowermost portion.

Therefore, a laser beam 101 of an annular shape, constituted by the two laser beams 14a and 24a superposed on each other, is substantially uniform in light intensity throughout the entire circumference thereof, and the circular image formed on the imaginary plane X has a uniform brightness throughout the entire circumference thereof.

The flaw detecting system comprises a photosensor 5, in addition to the above projector system 100. The photosensor 5 is disposed forwardly of the optical converter element 3, and is disposed on the axis L of the optical converter element 3. A lid 200 (i.e., an object to be detected) is disposed on a plane perpendicular to the axis L, and is disposed between the optical converter element 3 and the photosensor 5. The lid 200 is formed by pressing a flat metal plate, and has an annular recessed portion 201 of a considerable depth at its outer periphery. The recessed portion 201 is defined by an inner peripheral wall 202, an outer peripheral wall 203, and a bottom wall 204 interconnecting the walls 202 and 203. The bottom wall 204 is susceptible to a crack (flaw) during the formation of the lid 200, and therefore it is checked whether or not the bottom wall 204 has such a crack.

More specifically, the laser beam emitted from the optical converter element 3 is reflected by the inner surface of the outer peripheral wall 203 and is directed toward the bottom wall 204. If there is no crack in the bottom wall 204, the laser beam 101 is completely interrupted or blocked by the bottom wall 204, and therefore does not reach the photosensor 5. In contrast, if there is a crack in the bottom wall 204, part of the reflected laser beam 101 passes through this crack and reaches the photosensor 5, thus detecting the crack. A signal processing circuit connected to the photosensor 5, an alarm means, and etc., are well known in the art, and therefore explanation of these is omitted here.

FIG. 4 shows a modified form of the invention. Those parts of this embodiment corresponding respectively to those of the preceding embodiment of FIG. 1 are denoted by identical reference numerals, respectively, and explanation thereof are omitted here. A projector system 100 shown in FIG. 4 includes a collimator lens 50 disposed forwardly of an optical converter element 3 in coaxial relation thereto. The focus of the collimator lens 50 lies on the apex of the above-mentioned imaginary conical surface. A laser beam 101, coming from the optical converter element 3 and spreading out along this conical surface, is converted by the collimator lens 50 into a laser beam 102 of a circular shape advancing forwardly along an imaginary cylindrical surface having an axis aligned with the axis L of the optical converter element 3.

In the projector system of FIG. 4, a condenser lens 15 is disposed between a collimator lens 12 and a reflection mirror 13, and similarly a condenser lens 25 is disposed between a collimator lens 22 and a reflection mirror 23. The two condenser lenses 15 and 25 are equal in focal distance to each other, and the focal lengths of each of the condenser lenses 15, 25 is equal to the length of path of the laser beam from the condenser lens to the point of intersection between axes L1' and L2' of laser beams 14 and 24. Therefore, each of the laser beams 14 and 24 reflected respectively by the reflection mirrors 13 and 23 is directed toward the above point of intersection in a convergent manner. As a result, a laser beam 101 emitted from the optical converter element 3 is incident on the collimator lens 50 in such a manner that the width of the laser beam 101 in its radial direction increases progressively toward the collimator lens 50. Therefore, a laser beam 102 emitted from the collimator lens 50 has an unchanged radial width throughout the entire length thereof.

In the embodiment of FIG. 4, the laser beam 102 is applied directly to the bottom wall 204 of the lid 200. Therefore, whether or not any crack is present in the bottom wall 204 can be checked more accurately. A photosensor 5 has an annular shape corresponding to the shape of the bottom wall 204.

The fiber conduit, serving as the optical converter element 3 used in the projector systems 100 of FIGS. 1 and 4, may be replaced by a cylindrical lens.

The refractive index of a cylindrical lens 3 shown in FIGS. 5 and 6 is high at its radially central portion, and becomes lower progressively toward its outer periphery. Any those regions of the cylindrical lens 3 equidistant from the axis L of the cylindrical lens 3 have the same refractive index. As shown in FIG. 5, when one laser beam 14 is caused to be incident on the cylindrical lens 3, the cylindrical lens 3 emits a laser beam 14a which spreads out along a generally lower half (exceeding 180°) of the imaginary conical surface. Therefore, the image formed by the laser beam 14a on the imaginary plane X (see FIG. 1) constitutes a generally lower half of a circle having the center disposed on the axis L. When the other laser beam 24 is caused to be incident on the cylindrical lens 3, the cylindrical lens 3 emits a laser beam 24a which spreads out along a generally upper half (exceeding 180°) of the imaginary conical surface. The image formed by the laser beam 24a on the imaginary plane X constitutes a generally upper half of the above circle. Therefore, the two outgoing laser beams 14a and 24a partly overlapping each other, and jointly constitute a laser beam having a uniform light intensity over the entire circumference thereof.

As shown in FIG. 7, the cylindrical lens 3 may have a uniform refractive index over the entire transverse cross-sectional area thereof. In this case, when one laser beam 14 is incident on the cylindrical lens 3, a laser beam 14a emitted from the cylindrical lens 3 occupies part of the imaginary conical surface which is less than 180°. Therefore, by the use of the two laser beams 14 and 24 as in FIGS. 1 and 4, a laser beam emitted from the cylindrical lens 3 can not form an image of a complete circular shape on the imaginary plane. In this case, three or more laser beams are caused to be incident on the cylindrical lens 3. It is, of course, preferred that the laser beams be caused to be incident on the cylindrical lens 3 in such a manner that the laser beams are circumferentially spaced from one another at equal intervals.

In the case of the optical converter element 3 of FIG. 2 and the optical converter element 3 of FIG. 5, three or more laser beams may be caused to be incident on the optical converter element 3 in such a manner that the laser beams are circumferentially spaced from one another at equal intervals. With this arrangement, the laser beam emitted from the optical converter element 3 can h=more uniform in light intensity over the entire circumference thereof.

The present invention is not to be restricted to the above embodiments, and various modifications can be made. For example, although the reflection mirrors 13 and 23 are used in the embodiments of FIG. 1 and FIG. 4, they are replaced by prisms, respectively.

In the embodiments of FIG. 1 and FIG. 4, the reflection mirrors 13 and 23 may be omitted. In this case, the optical axes L1 and L2 of the laser beam-generating devices 1 and 2 are inclined at an angle of 20 with respect to the axis L of the optical converter element 3.

In the embodiments of FIG. 1 and FIG. 4, although the two laser beam-generating devices 1 and 2 are used, only one laser beam-generating device may be used. In this case, a light beam emitted from one light source is divided into a plurality of laser beams by a beam splitter such as a light semi-transmitting mirror, and the plurality of laser beams thus produced are caused by reflection means to be incident on the optical converter element.

In the projector systems according to the invention, the annular portion of the object to be checked may be of an oval shape. In this case, the annular (oval) portion are disposed in a plane inclined at an angle with respect to the axis L of the optical converter element.

What is claimed is:

1. A projector system comprising:
   (a) an optical converter element of a cylindrical shape for converting incident light, applied thereto, into outgoing light spreading out radially of said optical converter element, wherein said optical converter element comprises a large number of parallel optical fibers; and
   (b) light beam-generating means for generating a plurality of light beams, the optical axes of said plurality of light beams being spaced from one another in a direction of the circumference of said optical converter element and intersecting one another substantially at one point lying on the axis of said optical converter element, and the optical axes of said plurality of light beams being inclined at the same angle less than 90° with respect to the axis of said optical converter element so that, when said plurality of light beams are incident on said optical converter element, an outgoing light beam is emitted from said optical converter element such that said outgoing light beam extends along an imaginary conical surface coaxial with said optical converter element.

2. A projector system comprising:
   (a) an optical converter element of a cylindrical shape for converting incident light, applied thereto, into outgoing light spreading out radially of said optical converter element, wherein said optical converter element comprises a cylindrical solid lens; and
   (b) light beam-generating means for generating a plurality of light beams, the optical axes of said plurality of light beams being spaced from one another in a direction of the circumference of said optical converter element and intersecting one another substantially at one point lying on the axis of said optical converter element, and the optical axes of said plurality of light beams being inclined at the same angle less than 90° with respect to the axis of said optical converter element so that, when said plurality of light beams are incident on said optical converter element, an outgoing light beam is emitted from said optical converter element such that said outgoing light beam extends along an imaginary conical surface coaxial with said optical converter element.

3. A projector system according to claim 1, in which each of said plurality of light beams to be incident on said optical converter element is unchanged in cross-sectional area along the optical axis thereof, so that said outgoing light beam emitted from said optical converter element is uniform along its optical axis.

4. A projector system according to claim 1 or 2, further comprising a collimator lens coaxial with said optical converter element, said optical converter element being disposed between said light beam-generating means and said collimator lens, the focus of said collimator lens lying substantially on an apex of said imaginary conical surface, and when said light beam emitted from said optical converter element along said imaginary conical surface is incident on said collimator lens, a light beam being emitted from said collimator lens along an imaginary cylindrical surface coaxial with said collimator lens.

5. A projector system according to claim 4, in which said light beam-generating means comprises light source means for generating said plurality of light beams each substantially unchanged in cross-sectional area along the optical axis thereof, and a plurality of condenser lenses for respectively converging said light beams, generated from said light source, toward said optical converter element, the focal length of each of said condenser lenses being substantially equal to a length of path of said light beam from said condenser lens to the focus of said collimator lens, said outgoing light beam emitted from said optical converter element increasing in radial width progressively toward said collimator lens, and said light beam emitted from said collimator lens being substantially unchanged in radial width along the optical axis thereof.

6. A projector system according to claims 1 or 2, in which said plurality of light beams to be incident on said optical converter element are spaced from one another at equal intervals in the direction of the circumference of said optical converter element.

7. A projector system according to claim 1 or 2, in which said light beam-generating means comprises a plurality of light beam-generating devices, said plurality of light beam-generating devices comprising respective light sources for respectively generating light beams whose optical axes are parallel to one another, and respective reflection means for respectively reflecting said light beams, emitted respectively from said light sources, so as to direct said reflected light beams toward said optical converter element.

8. A projector system according to claim 1 or 2, in which said optical converter element further comprises a cylindrical clad in which said large number of optical fibers are embedded, said clad being lower in refractive index than said optical fibers.

9. A projector system according to claim 2, in which the refractive index of said cylindrical lens increases progressively from its radially central portion toward its outer periphery.

10. A projector system according to claim 2, in which said cylindrical lens has a uniform refractive index over the entire transverse cross-sectional area thereof.

11. A system for detecting a flaw in an annular portion of an object to be detected, comprising:
(a) an optical converter element of a cylindrical shape for converting incident light, applied thereto, into outgoing light spreading out radially of said optical converter element, wherein said optical converter element comprises a large number of parallel optical fibers;
(b) light beam-generating means for generating a plurality of light beams, optical axes of said plurality of light beams being spaced from one another in a direction of the circumference of said optical converter element and intersecting one another substantially at one point lying on the axis of said optical converter element, and the optical axes of said plurality of light beams being inclined at the same angle less than 90° with respect to the axis of said optical converter element, so that when said plurality of light beams are incident on said optical converter element, an outgoing light beam is emitted from said optical converter element so that said outgoing light beam extends along an imaginary conical surface coaxial with said optical converter element; and
(c) a photosensor disposed on one side of said optical converter element opposite to said light beam-generating means, the object to be detected being disposed between said optical converter element and said photosensor, said outgoing light beam emitted from said optical converter element being applied to the annular portion of said object, so that said photosensor detects part of said outgoing beam leaking through the flaw in said annular portion.

12. A system for detecting a flaw in an annular portion of an object to be detected, comprising:
(a) an optical converter element of a cylindrical shape for converting incident light, applied thereto, into outgoing light spreading out radially of said optical converter element, wherein said optical converter element comprises a cylindrical solid lens;
(b) light beam-generating means for generating a plurality of light beams, optical axes of said plurality of light beams being spaced from one another in a direction of the circumference of said optical converter element and intersecting one another substantially at one point lying on the axis of said optical converter element, and the optical axes of said plurality of light beams being inclined at the same angle less than 90° with respect to the axis of said optical converter element, so that when said plurality of light beams are incident on said optical converter element, an outgoing light beam is emitted from said optical converter element so that said outgoing light beam extends along an imaginary conical surface coaxial with said optical converter element; and
(c) a photosensor disposed on one side of said optical converter element opposite to said light beam-generating means, the object to be detected being disposed between said optical converter element and said photosensor, said outgoing light beam emitted from said optical converter element being applied to the annular portion of said object, so that said photosensor detects part of said outgoing beam leaking through the flaw in said annular portion.

13. A system for detecting a flaw in an annular portion of an object to be detected, comprising:
(a) an optical converter element of a cylindrical shape for converting incident light, applied thereto, into outgoing light spreading out radially of said optical converter element, wherein said optical converter element comprises a large number of parallel optical fibers;
(b) light beam-generating means for generating a plurality of light beams, optical axes of said plurality of light beams being spaced from one another in a direction of the circumference of said optical converter element and intersecting one another substantially at one point lying on the axis of said optical converter element, and the optical axes of said plurality of light beams being inclined at the same angle less than 90° with respect to the axis of said optical converter element, so that when said plurality of light beams are incident on said optical converter element, an outgoing light beam is emitted from said optical converter element so that said outgoing light beam extends along an imaginary conical surface coaxial with said optical converter element; and
(c) a collimator lens disposed on one side of said optical converter element opposite to said light beam-generating means, said collimator lens being coaxial with said optical converter element, the focus of said collimator lens lying substantially on an apex of said imaginary conical surface, and when said light beam emitted from said optical converter element along said imaginary conical surface is incident on said collimator lens, a light beam being emitted from said collimator lens along an imaginary cylindrical surface coaxial with said collimator lens; and
(d) a photosensor disposed on one side of said collimator lens opposite to said optical converter element, the object to be detected being disposed between said collimator lens and said photosensor, said light beam emitted from said collimator lens being applied to the annular portion of said object, so that said photosensor detects part of said light beam leaking through the flaw in said annular portion.

14. A system for detecting a flaw in an annular portion of an object to be detected, comprising:
(a) an optical converter element of a cylindrical shape for converting incident light, applied thereto, into outgoing light spreading out radially of said optical converter element, wherein said optical converter element comprises a cylindrical solid lens;

(b) light beam-generating means for generating a plurality of light beams, optical axes of said plurality of light beams being spaced from one another in a direction of the circumference of said optical converter element and intersecting one another substantially at one point lying on the axis of said optical converter element, and the optical axes of said plurality of light beams being inclined at the same angle less than 90° with respect to the axis of said optical converter element, so that when said plurality of light beams are incident on said optical converter element, an outgoing light beam is emitted from said optical converter element so that said outgoing light beam extends along an imaginary conical surface coaxial with said optical converter element; and (c) a collimator lens disposed on one side of said optical converter element opposite to said light beam-generating means, said collimator lens being coaxial with said optical converter element, the focus of said collimator lens lying substantially on an apex of said imaginary conical surface, and when said light beam emitted from said optical converter element along said imaginary conical surface is incident on said collimator lens, a light beam being emitted from said collimator lens along an imaginary cylindrical surface coaxial with said collimator lens; and (d) a photosensor disposed on one side of said collimator lens opposite to said optical converter element, the object to be detected being disposed between said collimator lens and said photosensor, said light beam emitted from said collimator lens being applied to the annular portion of said object, so that said photosensor detects part of said light beam leaking through the flaw in said annular portion.

* * * * *